(12) United States Patent
Hefetz et al.

(10) Patent No.: US 7,592,597 B2
(45) Date of Patent: Sep. 22, 2009

(54) METHOD AND APPARATUS FOR IMAGING WITH IMAGING DETECTORS HAVING SMALL FIELDS OF VIEW

(75) Inventors: Yaron Hefetz, Herzeliya (IL); Ira Blevis, Zichron Yaakov (IL)

(73) Assignee: GE Healthcare Israel, Tirat Hacarmel (IL)

( * ) Notice: Subject to any disclaimer, the term of this patent is extended or adjusted under 35 U.S.C. 154(b) by 265 days.

(21) Appl. No.: 11/498,630

(22) Filed: Aug. 3, 2006

(65) Prior Publication Data

US 2008/0029704 A1 Feb. 7, 2008

(51) Int. Cl.
G21K 1/02 (2006.01)
G01T 1/161 (2006.01)

(52) U.S. Cl. .............. 250/363.1; 250/363.01; 250/363.05; 250/363.08

(58) Field of Classification Search ............ 250/363.01, 250/363.05, 363.1, 505.1, 363.08
See application file for complete search history.

(56) References Cited

U.S. PATENT DOCUMENTS

| | | | |
|---|---|---|---|
| 5,198,680 A * | 3/1993 | Kurakake ................ 250/505.1 |
| 5,432,834 A * | 7/1995 | Gershman .................. 378/196 |
| 5,523,571 A * | 6/1996 | Velazquez et al. ...... 250/363.05 |
| 5,757,006 A | 5/1998 | DeVito et al. |
| 6,242,743 B1 | 6/2001 | DeVito et al. |
| 6,271,524 B1 | 8/2001 | Wainer et al. |
| 6,696,686 B1 | 2/2004 | Wainer et al. |
| 6,946,660 B2 | 9/2005 | El-Hanany et al. |
| 6,956,925 B1 | 10/2005 | Hoffman |
| 7,166,848 B2 | 1/2007 | El-Hanany et al. |
| 7,208,740 B2 | 4/2007 | El-Hanany et al. |
| 7,326,906 B2 | 2/2008 | Shalom et al. |
| 7,339,176 B2 | 3/2008 | El-Hanany et al. |
| 2003/0205676 A1* | 11/2003 | Nelson et al. .......... 250/370.09 |
| 2004/0262525 A1* | 12/2004 | Yunker et al. .......... 250/363.08 |
| 2005/0129295 A1 | 6/2005 | Shanmugam et al. |
| 2005/0218331 A1 | 10/2005 | Blevis et al. |
| 2005/0242292 A1 | 11/2005 | El-Hanany et al. |

(Continued)

FOREIGN PATENT DOCUMENTS

WO   WO 2005 118659 A2   12/2005

(Continued)

OTHER PUBLICATIONS

United States Statutory Invention Registration, Reg. No. H12, Published: Jan. 7, 1986, Inventors: Bennett et al., Assignee: The United States of America as represented by the United States Department of Energy, Washington, D.C., (13) pages.

*Primary Examiner*—David P Porta
*Assistant Examiner*—Mark R Gaworecki
(74) *Attorney, Agent, or Firm*—Dean D. Small; The Small Patent Law Group

(57) ABSTRACT

An apparatus for imaging a structure of interest comprises a plurality of imaging detectors mounted on a gantry. Each of the plurality of imaging detectors has a field of view (FOV), is independently movable with respect to each other, and is positioned to image a structure of interest within a patient. A data acquisition system receives image data detected within the FOV of each of the plurality of imaging detectors.

28 Claims, 5 Drawing Sheets

U.S. PATENT DOCUMENTS

| | | |
|---|---|---|
| 2006/0011852 A1 | 1/2006 | El-Hanany et al. |
| 2007/0040126 A1 | 2/2007 | El-Hanany et al. |
| 2007/0278387 A1 | 12/2007 | Shalom et al. |
| 2007/0295914 A1 | 12/2007 | El-Hanany et al. |
| 2008/0149842 A1 | 6/2008 | El-Hanany et al. |
| 2008/0237482 A1 | 10/2008 | Shahar et al. |
| 2008/0277591 A1 | 11/2008 | Shahar et al. |

FOREIGN PATENT DOCUMENTS

| | | |
|---|---|---|
| WO | WO 2005 119025 A2 | 12/2005 |
| WO | WO 2006 051531 A2 | 5/2006 |
| WO | WO 2006 054296 A2 | 5/2006 |

* cited by examiner

METHOD AND APPARATUS FOR IMAGING WITH IMAGING DETECTORS HAVING SMALL FIELDS OF VIEW

BACKGROUND OF THE INVENTION

This invention relates generally to nuclear medicine imaging, and more particularly, to efficiently imaging structures of interest with multiple imaging detectors having small fields of view.

In nuclear medicine (NM) imaging, the time required to acquire a scan of a patient can be long, leading to patient discomfort. Furthermore, if the patient moves, the image may be degraded and the scan may need to be repeated. In addition to the cost of the equipment, a high cost of operation may also be realized due to the time and manpower required to operate the equipment. Large size imaging detectors also have limited maneuverability due to their geometry when positioned close to a patient.

In some types of scans, such as when scanning the whole body or with large patients, the portion of the patient being imaged may require the entire field of view of a conventional large size imaging detector. However, when imaging a structure which is smaller than the field of view of the imaging detector, such as the heart, liver, kidney, or a tumor, portions of the imaging detector will acquire patient data outside of the structure of interest. Therefore, an effective sensitivity is decreased which is unrelated to collimator geometrical sensitivity, but rather refers to the opportunity lost by not collecting useful information.

Also, many types of scans require imaging from a number of axial positions around the patient. For example, conventional imaging detectors often acquire data while being rotated by a gantry around at least a portion of the patient, such as approximately 180 degrees and up to 360 degrees, to obtain sufficient data of the structure for volumetric imaging and processing. This is time consuming, which limits patient through-put, and is prone to error due to patient movement as discussed above.

Therefore, a need exists for methods and apparatus to decrease the time needed to acquire image data of smaller structures during NM imaging. Certain embodiments of the present invention are intended to meet these needs and other objectives that will become apparent from the description and drawings set forth below.

BRIEF DESCRIPTION OF THE INVENTION

In one embodiment, an apparatus for imaging a structure of interest comprises a plurality of imaging detectors mounted on a gantry. Each of the plurality of imaging detectors has a field of view (FOV), is independently movable with respect to each other, and is positioned to image a structure of interest within a patient. A data acquisition system receives image data detected within the FOV of each of the imaging detectors.

In another embodiment, a method for acquiring images of a structure of interest with a plurality of imaging detectors comprises positioning a plurality of imaging detectors proximate to a structure of interest. Each of the plurality of imaging detectors has a FOV and is independently movable with respect to each other to change the FOV. At least a sub-set of the imaging detectors are aimed to image at least a portion of the structure of interest within the FOV. Image data is acquired with at least the sub-set of the plurality of imaging detectors, and the image data received from each of the imaging detectors is combined to form a composite image.

In another embodiment, an apparatus for imaging a structure of interest comprises a plurality of imaging detectors mounted on a gantry. Each of the plurality of imaging detectors has a field of view (FOV) and is independently movable with respect to each other to change the FOV. At least a sub-set of the plurality of imaging detectors is positioned to image a structure of interest within a patient. A plurality of configurable collimators are mounted to the plurality of imaging detectors, and a data acquisition system receives image data detected within the FOV of the plurality of imaging detectors.

Figure 1:
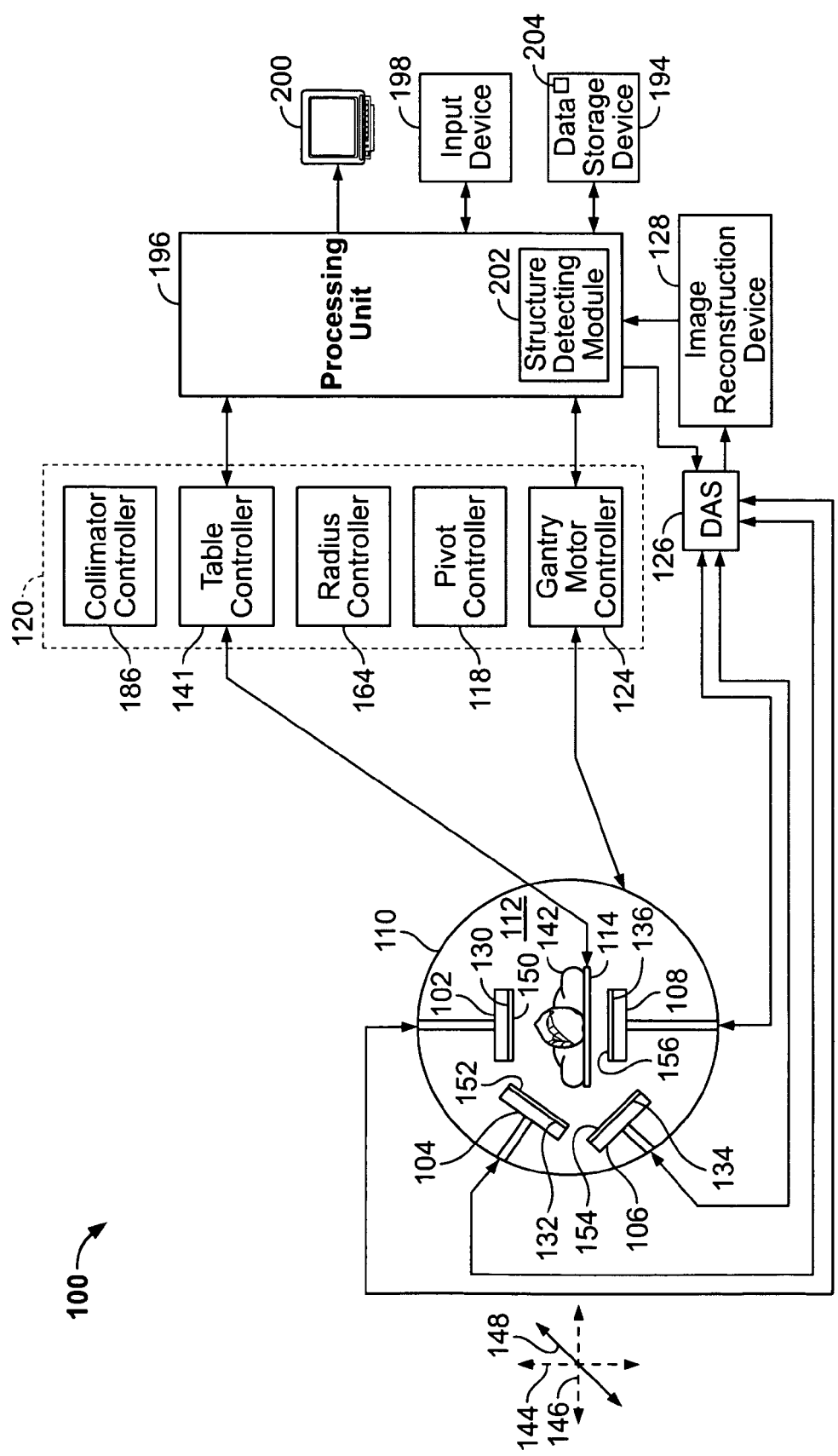
FIG. 1 is a schematic illustration of a Nuclear Medicine (NM) imaging system which has a plurality of small imaging detectors mounted on a gantry in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed imaging software package, and the like. It should be understood that the various embodiments are not limited to the arrangements and instrumentality shown in the drawings.

DETAILED DESCRIPTION OF THE INVENTION

FIG. 1 is a schematic illustration of a Nuclear Medicine (NM) imaging system 100 which has a plurality of small imaging detectors mounted on a gantry. In FIG. 1, first, second, third through N imaging detectors 102, 104, 106 and 108 are mounted on a gantry 110. As illustrated in FIG. 1, N is equal to four; however, it should be understood that two, three or more than four imaging detectors may be used.

Each of the first through N imaging detectors 102-108 are smaller than a conventional imaging detector. A conventional imaging detector may be large enough to image most or all of a width of a patient's body at one time and may have a diameter of approximately 40 cm. In contrast, each of the first through N imaging detectors 102-108 may have dimensions of 4 cm to 20 cm and may be formed of cadmium zinc telluride (CZT) tiles. For example, each of the first through N imaging detectors 102-108 may be 8×8 cm in size and be composed of a plurality of CZT pixilated modules (not shown). For example, each module may be 4×4 cm in size and have 16×16=256 pixels. It should be understood that the first through N imaging detectors 102-108 may be different sizes and/or shapes with respect to each other, such as square, rectangular, circular or other shape. An actual field of view (FOV) of each of the first through N imaging detectors 102-108 may be directly proportional to the size and shape of the respective imaging detector.

The gantry 110 may be formed with an aperture 112 therethrough as illustrated. A patient table 114 is configured with a support mechanism (not shown) to support and carry a patient 142 in a plurality of viewing positions within the aperture 112 and relative to the first through N imaging detectors 102-108. Alternatively, the gantry 110 may comprise a plurality of gantry segments (not shown), each of which may independently move one imaging detector or a subset of imaging detectors. The gantry 110 may also be configured in other shapes, such as a "C" and "L", for example, and may be rotatable about the patient 142. For example, the gantry 110 may be formed as a closed ring or circle, or as an open arc or arch which allows the patient 142 to be easily accessed while imaging and facilitates loading and unloading of the patient 142, as well as reducing claustrophobia in susceptible patients 142.

Additional imaging detectors (not shown) may be positioned to form an arc or ring around the patient 142. Alternatively, more than one ring, arc or arch may be formed. By positioning multiple imaging detectors at multiple positions with respect to the patient 142, image data specific to a structure of interest within the patient 142 may be acquired more quickly compared to acquisitions using conventional large size detectors.

Optionally, imaging detectors may be arranged around the patient 142 in a closed pack formation. Optionally, imaging detectors may be arranged around the patient 142 in a plurality of axial locations. When imaging the heart, for example, two, three, four or more arches of imaging detectors may be used. Each arch may span 90 to 270 degrees around the patient 142, and together cover a substantial portion of the torso. For example, three arches configured using 8×8 cm sized imaging detectors would form a curved band of over 24 cm in width (taking into account some, preferably minimal, gap between imaging detectors).

Each of the first, second, third through N imaging detectors 102, 104, 106 and 108 has a radiation detection face 130, 132, 134 and 136, respectively, which is directed towards a structure of interest within the patient 142. The radiation detection faces 132, 132, 134 and 136 are each covered by a collimator 150, 152, 154 and 156, respectively. The actual FOV for each of the first through N imaging detectors 102-108 may be increased, decreased, or relatively unchanged by the type of collimator 150-156, such as pinhole, parallel-beam converging, diverging fan-beam, converging or diverging cone-beam, multi-bore, multi-bore converging, multi-bore converging Fan-Beam, multi-bore converging Cone-Beam, multi-bore diverging, or other type of collimator.

Optionally, multi-bore collimators may be constructed to be registered with pixels of a pixilated detector such as CZT pixilated detector. Registered collimation may increase spatial resolution by forcing photons going through one bore to be collected primarily by one pixel. Additionally, registered collimation may increase sensitivity and energy response of pixilated detectors as detector area near the edges of a pixel or in-between two adjacent pixels may have reduced sensitivity or decreased energy resolution or other performance degradation. Having collimator septa directly above the edges of pixels reduces the chance of photon impinging at these degraded-performance locations, without decreasing the overall probability of a photon passing through the collimator.

A controller unit 120 may control the movement and positioning of the patient table 114, the gantry 110, the first through N imaging detectors 102-108, and the collimators 150-156. A range of motion during an acquisition or between images is set to keep the actual FOV of each of the first through N imaging detectors 102-108 directed towards or "aimed at" the structure of interest. The range of motion may be based on fixed or patient specific orbits, and small motions, such as detector "dither", may be used. Optionally, the amount or range of motion may be based on a preliminary image of the structure of interest. The preliminary image may be obtained by the imaging system 100, or by a previously obtained image, optionally from another, optionally different type of imaging system. For example, a CT image may be used as the preliminary image.

The controller unit 120 may have a gantry motor controller 124, table controller 141, radius controller 164, pivot controller 118, and collimator controller 186. The controllers 118, 124, 141, 164 and 186 may be automatically commanded by a processing unit 196, manually controlled by an operator, or a combination thereof. The gantry motor controller 124 may rotate the first through N imaging detectors 102-108 with respect to the patient 142 individually in segments or simultaneously in a fixed relationship to one another. Optionally, a mechanical link or links connected to plurality or sub-set of the imaging detectors may move the plurality of imaging detectors in unison. The table controller 141 may move the patient table 114 to position the patient 142 relative to the FOV of one or more of the first through N imaging detectors 102-108. The patient table 114 may be moved in up-down direction 144, in-out direction 148, and right-left direction 146, for example. The radius controller 164 may move each of the first through N imaging detectors 102-108 closer to and further from a surface of the patient 142, and the pivot controller 118 may move the first through N imaging detectors 102-108 axially with respect to the patient 142. The collimator controller 186 may adjust a position of an adjustable collimator, such as a collimator with adjustable strips (or vanes) or adjustable pinhole(s). It should be noted that motion of one or more imaging detectors may be in directions other than strictly axially or radially, and optionally, motions in several motion directions may be combined to create the desired motion. Therefore, the term "motion controller" may be used to indicate a collective name for all motion controllers.

Prior to acquiring an image of the structure of interest, the first through N imaging detectors 102-108, gantry 110, patient table 114 and/or collimators 150-156 may be adjusted as discussed above to first or initial imaging positions. The first through N imaging detectors 102-108 may each be positioned to image all or a portion of the structure depending on the size of the structure, area(s) of greater interest within the structure, position of the structure within the patient 142, and the like. Alternatively, one or more of the imaging detectors 102-108 may not be used to acquire data if not needed. Positioning may be accomplished manually by the operator and/ or automatically, such as by using edge detection, prior knowledge of the patient's anatomy, a pre-acquired attenuation map, or by calculating projection views of the structure of interest from an image taken before the current acquisition, such as by another imaging modality such as CT, MRI, X-Ray, SPECT, PET or ultrasound, or with the preliminary image discussed above. Optionally, a planar image or a lower quality image with lower resolution or a low count total may be used to position the patient 142 either manually or automatically. Alternatively, a persistence image that measures the count rate may be used.

After the first through N imaging detectors 102-108, gantry 110, patient table 114, and collimators 150-156 are initially positioned, one or more images are acquired by each imaging detector being used. The image data acquired by each imaging detector may be combined and reconstructed into a composite image, which may comprise 2 dimensional (2D) images, a 3 dimensional (3D) volume or a 3D volume over time (4D).

In one embodiment, the first through N imaging detectors 102-108, gantry 110, patient table 114, and collimators 150-156 remain stationary after being initially positioned. In another embodiment, an effective field of view for one or more of the imaging detectors may be increased by movement such as pivoting one or more of the first through N imaging detectors 102-108, rotating one or more of the first through N imaging detectors 102-108 with the gantry 110, adjusting one or more of the collimators 150-156, or moving the patient table 114.

A data acquisition system (DAS) 126 receives the electrical signal data produced by the first through N imaging detectors 102-108 and converts this data into digital signals for subsequent processing. An image reconstruction device 128, a data storage device 194 and a processing unit 196 may also be provided. It should be noted that one or more functions related to one or more of data acquisition, motion control, data processing and image reconstruction may be accomplished through software and by shared processing resources which may be located within or near the imaging system 100, or may be located remotely.

Figure 2:
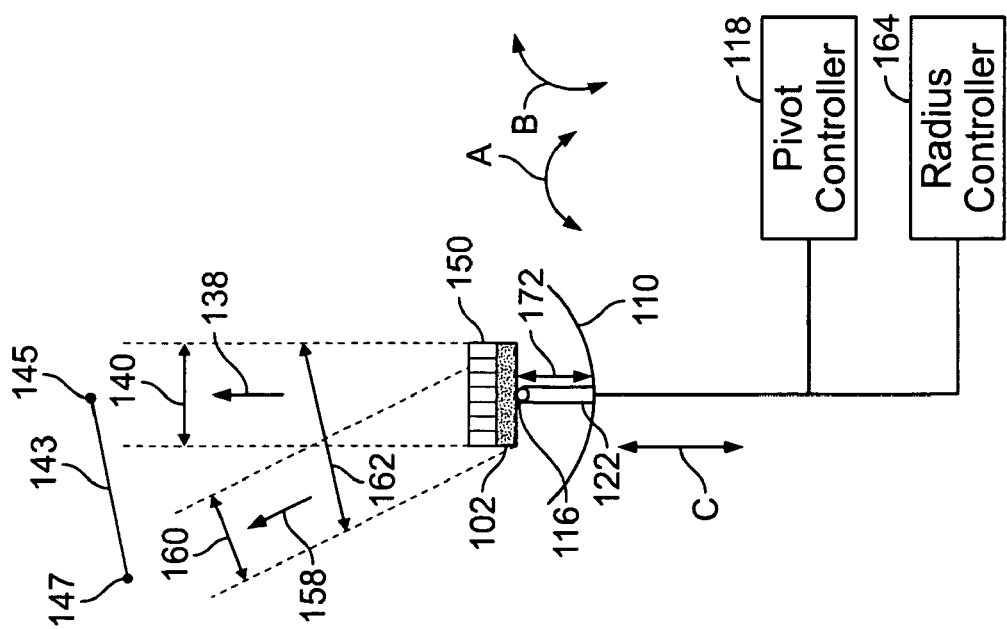
FIG. 2 illustrates pivoting motion used to increase the effective field of view (FOV) of the first imaging detector in accordance with an embodiment of the present invention.

FIG. 2 illustrates pivoting motion used to increase the effective FOV of the first imaging detector 102. It should be noted that detector motion or reorientation may also increase the sampling of the imaging data. Having a largely sampled dataset may improve reconstruction and may reduce artifacts. By pivoting the first imaging detector 102, data can be collected from an area larger than the actual FOV. Each of the first through N imaging detectors 102-108 may be pivoted to change the direction from which the respective radiation detecting face 130 senses radiation.

The first imaging detector 102 may be mounted on a pivot 116 and leg 122. Other pivoting mechanisms may be used. The pivot controller 118 may command the pivot 116 to move along arrow A, along arrow B (which is orthogonal to arrow A), or any position between the arrows A and B. The pivoting motion may be used together with one or more of the other movements previously discussed.

A pivot range 143 for each of the first through N imaging detectors 102-108 may be determined. For example, when imaging a structure that is larger than the actual FOV of the first imaging detector 102, the pivot range 143 may have a start point 145 at one end wherein the FOV images one outer edge of the structure. Optionally, a predefined amount of surrounding tissue may be imaged. An end point 147 of the pivot range 143 may be set to image an opposite outer edge of the structure as well as a predefined amount of surrounding tissue. Therefore, a unique pivot range 143 may be defined for each of the imaging detectors that may be specific to a particular scan.

Alternatively, one or more of the first through N imaging detectors 102-108 may be moved through a fixed, predetermined pivot range 143. A rate or speed of pivoting may also be predetermined, set by an operator, or determined based on the anatomy being scanned, size of the structure, level of radiation detected, and the like. It should be noted that rate of pivoting need not be constant throughout the pivot range 143, may be different for a different axis of pivoting, and may be different for different imaging detectors or throughout the duration of the acquisition. For example, the rate of pivoting may be higher during parts of the pivoting range 143 wherein the first imaging detector 102 is aimed at the surrounding tissue. Thus, the first imaging detector 102 collects more data from the structure of interest than from the surrounding tissue.

According to an exemplary embodiment of the invention, the first imaging detector 102 may acquire image data at a first position 138 corresponding to the start point 145 of the pivot range 143. Actual FOV 140 of the first imaging detector 102 is dependent in part upon the collimator 150. The first imaging detector 102 is pivoted through the pivot range 143 along the direction of arrow A to a second position 158 corresponding to the end point 147 with actual FOV 160. An effective FOV 162 that is larger than either of the actual FOVs 140 and 160 is formed. The first imaging detector 102 may continuously acquire data while pivoting from the first position 138 to the second position 158. Alternatively, the first imaging detector 102 may acquire a series of images as the pivot controller 118 moves the imaging detector through the pivot range 143. Alternatively, the pivot controller 118 may move the first imaging detector 102 to a predetermined number of positions within the pivot range 143, and the first imaging detector 102 acquires images at each of the positions. Although the example is illustrated in a single dimension, it should be understood that the effective field of view may be increased by pivoting the first imaging detector 102 in other directions.

The leg 122 may be commanded by the radius controller 164 to move the first imaging detector 102 towards and away from the patient 142 along arrow C. Distance 172 may thus be changed to increase or decrease the distance from the patient 142. The leg 122 may be piston driven, spring loaded, chain driven, or any other type of actuator. Alternatively, the leg 122 may be mounted on a segment (not shown) of the gantry 110, and thus the segment may also be driven in the direction of arrow C. The radius may be changed while acquiring data or between acquisitions, and may be used in combination with other motions. Anti-collision software and/or sensors (not shown) may also be used to ensure that the patient 142 does not collide with the first through N imaging detectors 102-108.

Figure 3:
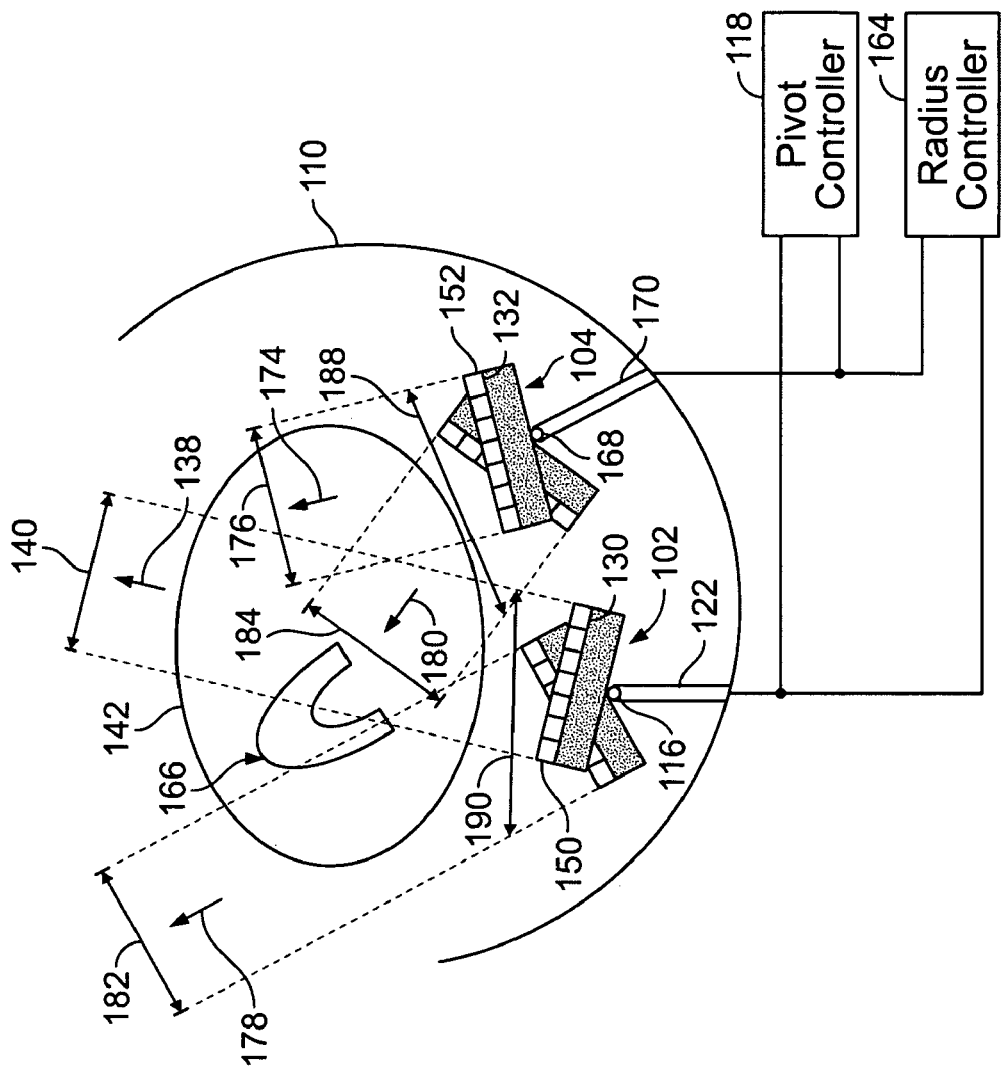
FIG. 3 illustrates the first and second imaging detectors of FIG. 1 using pivoting motion to increase an effective FOV to scan a structure of interest in accordance with an embodiment of the present invention.

FIG. 3 illustrates the first and second imaging detectors 102 and 104 of FIG. 1 using pivoting motion to increase an effective FOV to scan a structure of interest 166. In this example, the structure of interest 166 may be the heart within the patient 142. Although the first and second imaging detectors 102 and 104 are illustrated in one-dimension, as stated previously the radiation detecting faces 130 and 132 each have a two-dimensional FOV. Like item numbers with respect to FIG. 2 will be used.

The collimators 150 and 152 are mounted proximate the radiation detecting faces 130 and 132. In this example, the collimators 150 and 152 are parallel beam collimators and therefore the actual FOVs of the first and second imaging detectors 102 and 104 are approximately equal to the actual or active size of the imaging detector.

The first imaging detector 102 is mounted on the pivot 116 which is interconnected to the gantry 110 by the leg 122 as discussed in FIG. 2. The second imaging detector 104 is similarly mounted on a pivot 168 which is interconnected to the gantry 110 by a leg 170. The pivot controller 118 and radius controller 164 controls the motion of the first and second imaging detectors 102 and 104 separately, and thus may move or swing the first imaging detector 102 in a direction different from the second imaging detector 104. The first and second imaging detectors 102 and 104 may also be moved at different rates with respect to each other as well as during the acquisition.

The first imaging detector 102 acquires a first image at the first position 138 which has the actual FOV 140. At the same time, the second imaging detector 104 acquires a first image at a first position 174 having an actual FOV 176. The first and second imaging detectors 102 and 104 are pivoted from the first positions 138 and 174 through Nth positions 178 and 180 which have actual FOVs 182 and 184, respectively. Effective FOV 188 is greater than the actual FOVs 176 and 184 of the first imaging detector 102 and effective FOV 190 is greater than the actual FOVs 140 and 182 of the second imaging detector 104, and thus more data is acquired of the structure of interest 166 and surrounding tissue.

Additional imaging detectors may be positioned around a portion or all of the patient 142 to acquire data of the structure of interest 166 simultaneously with the first and second imaging detectors 102 and 104. The acquired data may be combined into a single composite dataset, and may be acquired in a shorter amount of time compared to a larger field of view detector.

Figure 4:
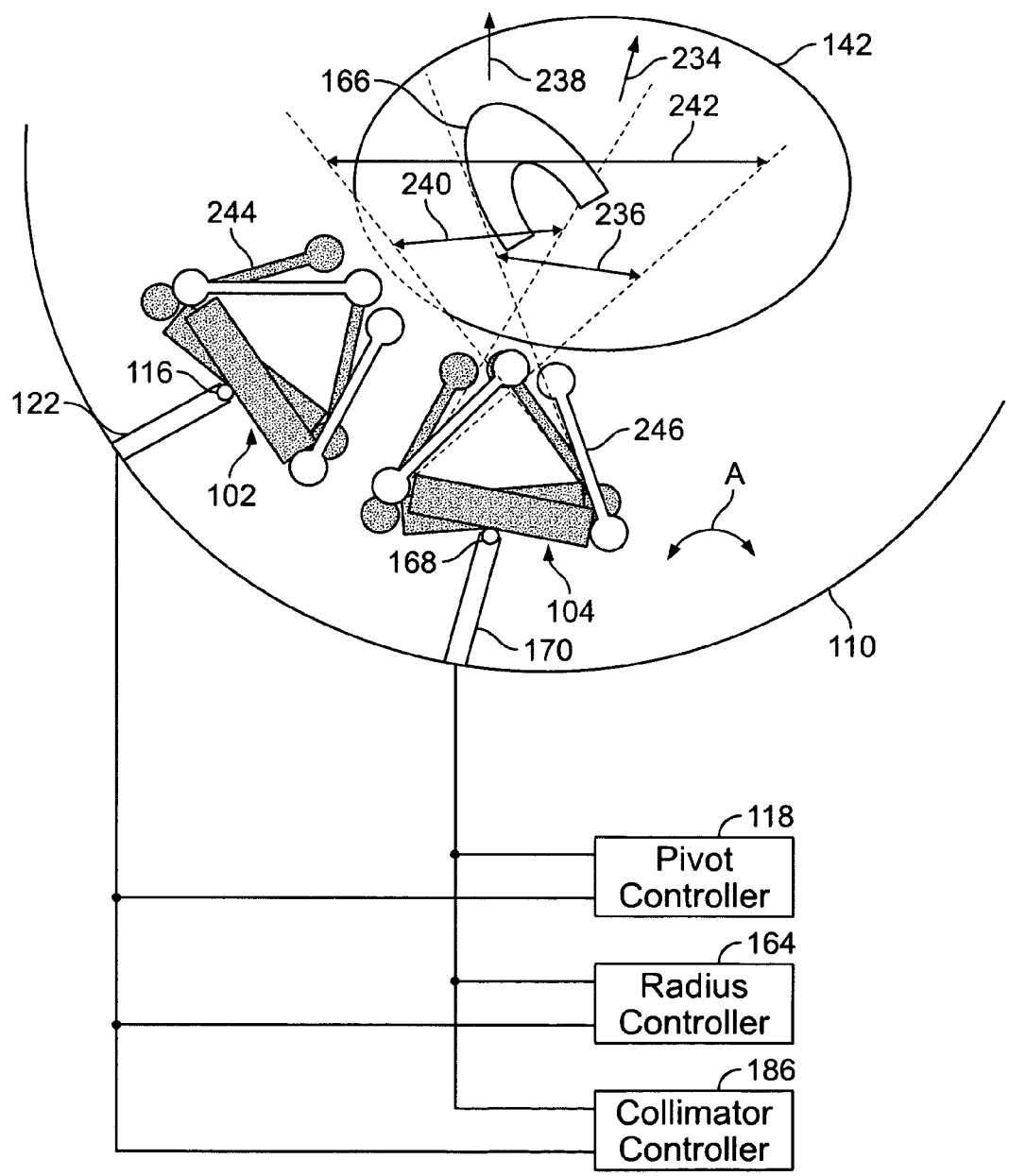
FIG. 4 illustrates the first and second imaging detectors of FIG. 1 with pinhole collimators attached thereto in accordance with an embodiment of the present invention.

FIG. 4 illustrates the first and second imaging detectors 102 and 104 of FIG. 1 with pinhole collimators 244 and 246, respectively, attached thereto. The pinhole collimators 244 and 246 illustrated have a single pinhole, and an actual FOV is defined by the pinhole geometry. The first and second imaging detectors 102 and 104 are mounted to the gantry 110 as discussed in FIG. 3 and are interconnected with, and driven by, the pivot controller 118 and the radius controller 164. As discussed previously, an effective FOV which is larger than the actual FOV may be achieved by pivoting the first and second imaging detectors 102 and 104. The second imaging detector 104 will be discussed, although it should be understood that the first imaging detector 102, as well as any other imaging detectors installed on the gantry 110, may be operated in a similar fashion to simultaneously acquire patient data.

The second imaging detector 104 acquires a first image at the first position 234 which has actual FOV 236. The pivot controller 118 pivots the second imaging detector 104 from the first position 234 toward the Nth position 238 along the arrow A. One or more images may be acquired between the first and Nth positions 234 and 238. The pivot controller 118 may stop the pivot motion during acquisition, or data may be acquired while the second imaging detector 104 is being pivoted. The FOV of the second imaging detector 104 is expanded from the actual FOV 236 to an effective FOV 242. As data is acquired from multiple positions around or proximate the patient 142, data of the structure of interest 166 is collected faster and the acquisition time during which the patient 142 must remain without moving is shorter. A shorter data acquisition time also increases patient throughput and thus enables more efficient utilization of the imaging system 100, the clinic's space and operating personnel, and thus decreases the cost per image.

In addition, the collimator controller 186 may move the location of the pinhole of the pinhole collimator 246. Changing the position of the pinhole changes the actual FOV and thus the effective FOV. Alternatively, collimators having multiple pinholes which are configurable may be mounted to the first and second imaging detectors 102 and 104. The collimator controller 186 may control the position of the multiple pinholes for each multi-pinhole collimator separately. It should be noted that motion of the first and second detectors 102 and 104 relative to a stationary pinhole also causes the FOV to change and/or move. Additionally, changing the distance between the collimator or the pinhole(s) of the collimator and the detector changes the size of the FOV.

Figure 5:
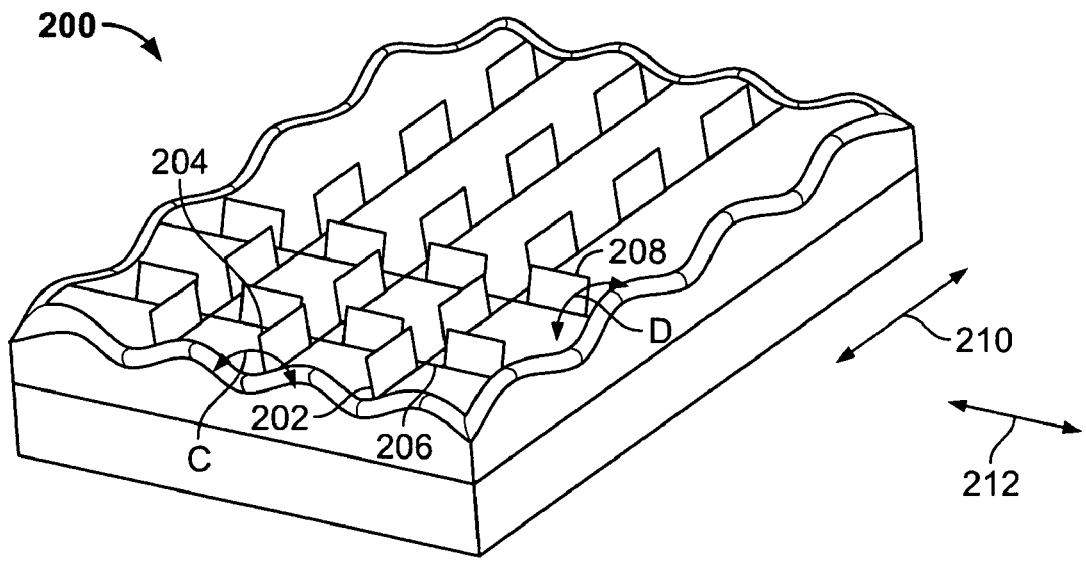
FIG. 5 illustrates an adjustable collimator with variable geometry which may be used to increase the effective FOV of the first through N imaging detectors of FIG. 1 in accordance with an embodiment of the present invention.

FIG. 5 illustrates an adjustable collimator 200 with variable geometry which may be used to increase the effective FOV of the first through N imaging detectors 102-108 of FIG. 1. The adjustable collimator 200 may be formed of a material such as tungsten. Flat sheets of tungsten are cut into strips or vanes with material periodically removed to form a comb structure. Strips 202 and 204 are arranged parallel to one another along a first direction 210. Strips 206 and 208 are arranged parallel to one another along a second direction 212, which may be, but are not required to be, perpendicular to the first direction 210. Many strips 202-208 may be used. The areas of removed material allow the position of the strips 202 and 204 to be varied along the direction of arrow C and the position of the strips 206 and 208 may be varied along the direction of arrow D. Alternatively, the adjustable collimator 200 may be constructed such that one set of parallel strips are held stationary while a second set of strips, configured at an angle to the first set of strips, are capable of being tilted. This configuration allows scanning the FOV by changing one dimension.

Figure 6:
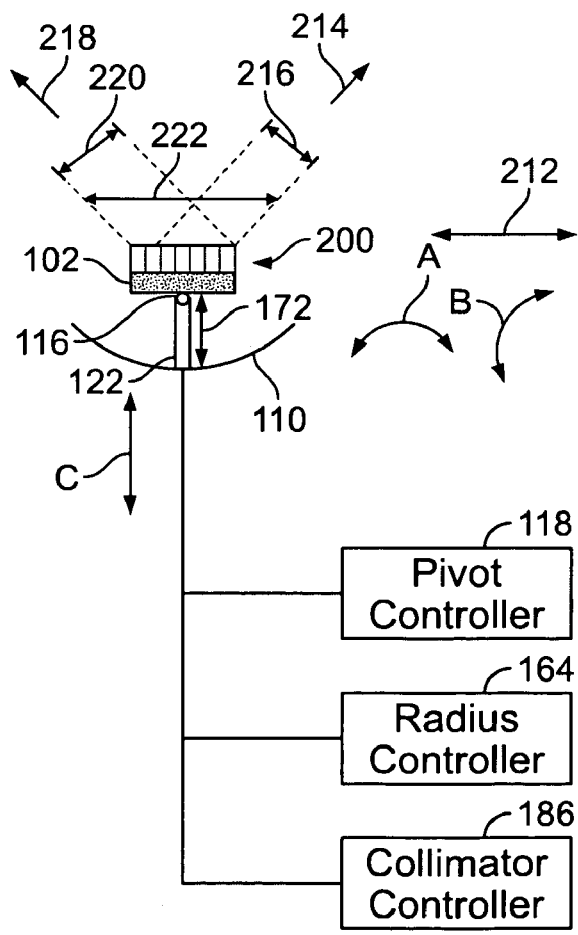
FIG. 6 illustrates the adjustable collimator of FIG. 5 mounted on the first detector in accordance with an embodiment of the present invention.

FIG. 6 illustrates the adjustable collimator 200 of FIG. 5 mounted on the first imaging detector 102. The collimator controller 186 may be used to control the geometry of the adjustable collimator 200 by controlling the movement of the strips 202-208. Referring also to FIG. 5, the collimator controller 186 may move the strips 202 and 204 along the path of arrow C to a first position 214 for actual FOV 216. The collimator controller 186 may move the strips 202 and 204 in an opposite direction along the path of arrow C to an Nth position 218 for actual FOV 220. Similarly, the collimator controller 186 may move the strips 206 and 208 along the path of arrow D to achieve a larger effective FOV along the first direction 210. By adjusting the positions of the strips 202, 204, 206 and 208, a much larger effective FOV 222 may be achieved. Therefore, the first imaging detector 102 may be used to scan a larger area, such as a torso of the patient 142.

Figure 7:
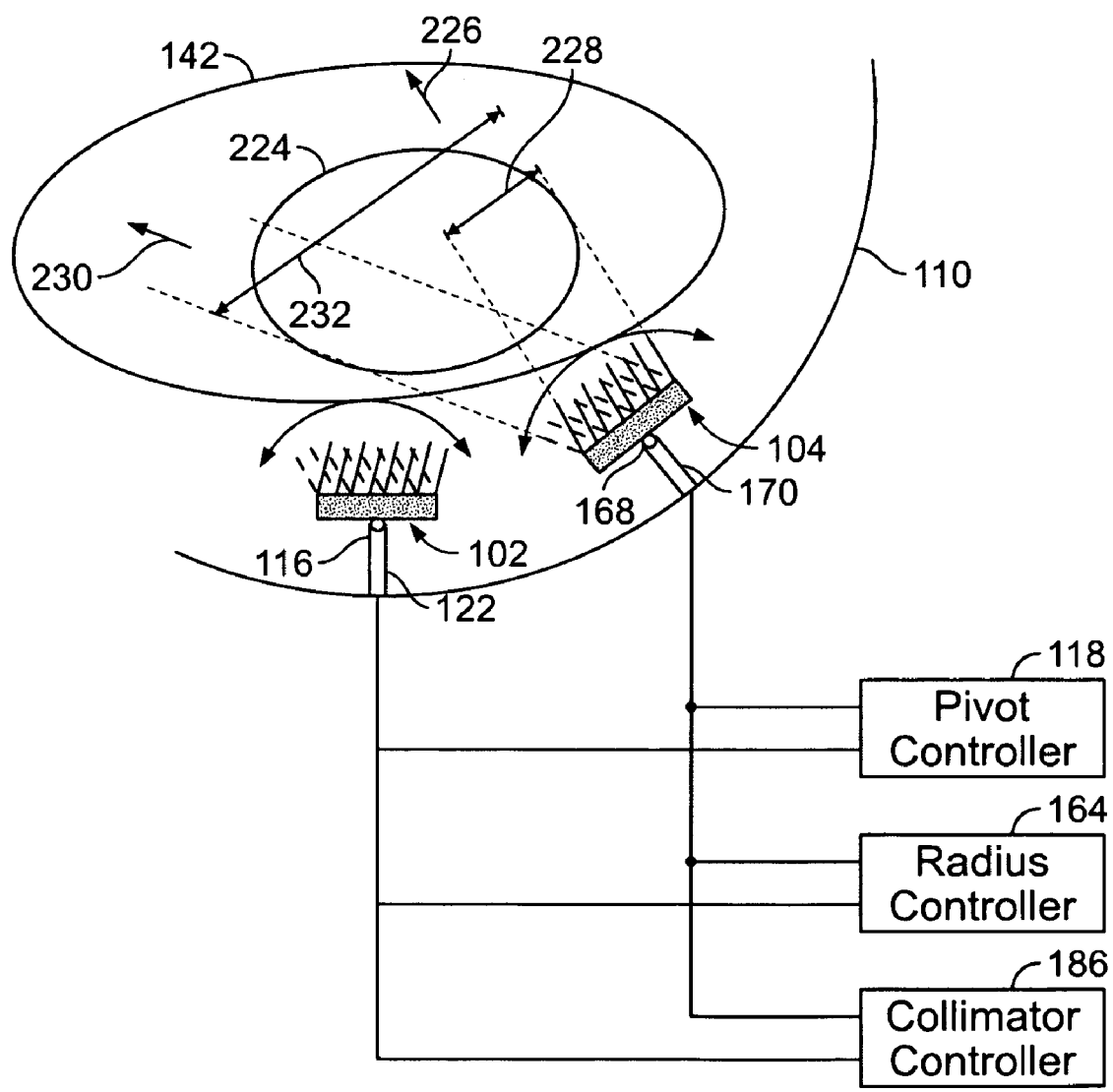
FIG. 7 illustrates the first and second imaging detectors of FIG. 1 having the adjustable collimators of FIG. 5 mounted thereon in accordance with an embodiment of the present invention.

FIG. 7 illustrates the first and second imaging detectors 102 and 104 of FIG. 1 having the adjustable collimators 200 of FIG. 5 mounted thereon. Structure of interest 224 within the patient 142 is larger than the actual FOVs of the first and second imaging detectors 102 and 104. By changing the geometry of the adjustable collimators 200, the effective FOV may be increased to be greater than the actual FOV.

The first and second imaging detectors 102 and 104 are mounted on the pivots 116 and 168, respectively, which are interconnected to the gantry 110 by the legs 122 and 170 as discussed in FIG. 2. The pivot controller 118 and radius controller 164 may be used as discussed above to further increase the effective FOV. The positioning and movement of the imaging detectors 102 and 104 are separate, and thus each the first and second imaging detector 102 and 104 may be positioned in an optimal scanning location.

The second imaging detector 104 may acquire a first image at a first position 226 that has an actual FOV 228. The first position 226 may define one or more of a collimator position, an angle with respect to the pivot 168, a radius, an axial position with respect to the gantry 110, and the like. The collimator controller 186 moves all or a sub-set of the strips 202-208 through their range of motion to Nth position 230 to form an effective FOV 232. The collimator controller 186 may move the strips 202-208 predetermined distances, stop, and then acquire an image before moving the strips 202-208 to a next imaging position. Alternatively, the collimator controller 186 may move the strips 202-208 in a smooth sweeping motion, acquiring a single image across the effective FOV 232. The effective FOV 232 may be further increased by pivoting the second imaging detector 104 with the pivot controller 118.

A technical effect of the invention is efficiently imaging a structure of interest with an imaging system that has a plurality of imaging detectors with FOVs which may be smaller than the structure of interest. Each of the plurality of imaging detectors is small and may be separately positioned relative to the patient. The plurality of imaging detectors acquire images of the structure from different locations around the patient, and thus image data relevant to the structure of interest is acquired in a shorter period of time than with conventional large imaging detectors. Movement may be used during or between acquisitions to increase the effective FOV. The imaging detectors may be moved by pivoting axially and moving radially towards and away from the patient; the gantry may be rotated; adjustable collimators may be adjusted by moving pinhole(s) and/or strips; and/or the patient table may be moved.

While the invention has been described in terms of various specific embodiments, those skilled in the art will recognize that the invention can be practiced with modification within the spirit and scope of the claims.

What is claimed is:

1. An apparatus for imaging a structure of interest, comprising:
    a plurality of imaging detectors mounted on a gantry, each of the plurality of imaging detectors having a field of view (FOV), each of the plurality of imaging detectors being independently movable with respect to each other, the plurality of imaging detectors being positioned to image a structure of interest within a patient;
    a data acquisition system for receiving image data detected within the FOV of each of the plurality of imaging detectors; and
    a plurality of pivots interconnecting the gantry and the plurality of imaging detectors, at least one of the plurality of imaging detectors movable at a pivot point in two different directions transverse to each other.

2. The apparatus of claim 1, wherein the plurality of imaging detectors include at least three imaging detectors that are mounted on the gantry in at least one of an arc and a circle proximate to the patient.

3. The apparatus of claim 1, further comprising a plurality of adjustable collimators mounted on the plurality of imaging detectors, each of the plurality of adjustable collimators being adjustable with respect to the imaging detectors to define and adjust the FOV between first and second collimation positions.

4. The apparatus of claim 1, further comprising a plurality of collimators mounted on the plurality of imaging detectors, wherein at least one of the plurality of collimators is a multi-bore collimator, a multi-bore converging collimator, a multi-bore converging Fan-Beam collimator, a multi-bore converging Cone-Beam collimator, a multi-bore diverging collimator, and a pinhole collimator.

5. The apparatus of claim 1, wherein each of the plurality of pivots at least one of allowing and controlling pivoting motion of the plurality of imaging detectors to change the FOV.

6. The apparatus of claim 1, further comprising:
    a pivot controller for moving at least one of the plurality of pivots along at least one axis to change the FOV of at least one of the plurality of imaging detectors while acquiring the image data.

7. The apparatus of claim 1, further comprising:
    a plurality of configurable collimators mounted and adjustable relative to the plurality of imaging detectors; and
    a collimator controller adjusting at least one of the plurality of configurable collimators, between first and second collimation positions, to change the FOV of at least one of the plurality of imaging detectors.

8. An apparatus in accordance with claim 1, wherein at least one of the plurality of imaging detectors is movable at a single pivot point in two different directions transverse to each other.

9. An apparatus in accordance with claim 1, wherein at least one of the plurality of imaging detectors has a radiation detection face and an opposed mounting face opposite the radiation detection face, the pivot point located at the mounting face.

10. An apparatus in accordance with claim 1, wherein at least one of the plurality of imaging detectors has a radiation detection face and an opposed mounting face opposite the radiation detection face, a mounting leg is coupled to the mounting face at the pivot point to enable the at least one imaging detector to move in two directions transverse to each other to change the FOV.

11. An apparatus in accordance with claim 1, wherein at least one of the plurality of imaging detectors has a radiation detection face and an opposed mounting face opposite the radiation detection face, a hydraulically actuated mounting leg is coupled to the mounting face at the pivot point to enable the at least one imaging detector to move in two directions to change the FOV.

12. An apparatus in accordance with claim 1, wherein at least one of the plurality of imaging detectors has a radiation detection face with a size of no more than 20 centimeters by 20 centimeters.

13. An apparatus in accordance with claim 1, wherein at least one of the plurality of imaging detectors has a radiation detection face with a size of no more than 8 centimeters by 8 centimeters.

14. An apparatus in accordance with claim 1, wherein at least one of the plurality of imaging detectors includes at least four pixilated modules, at least one of the pixilated modules has a detection face of no more than 4 centimeters by 4 centimeters.

15. An apparatus in accordance with claim 1, wherein at least one of the plurality of imaging detectors includes at least four pixilated modules, at least one of the pixilated modules has a plurality of cadmium zinc telluride (CZT) detectors.

16. A method for acquiring images of a structure of interest with a plurality of imaging detectors, comprising:
    positioning a plurality of imaging detectors proximate to a structure of interest, each of the plurality of imaging detectors having a field of view (FOV), at least one of the plurality of imaging detectors being independently movable at a pivot point in two different directions transverse to each other to change the FOV;
    aiming at least a sub-set of the plurality of imaging detectors to image at least a portion of the structure of interest within the FOV;

acquiring image data with at least the sub-set of the plurality of imaging detectors; and
combining the image data received from the plurality of imaging detectors to form a composite image.

17. The method of claim 16, the aiming further comprising adjusting a position of each of the plurality of imaging detectors independently of one another to change the FOV.

18. The method of claim 16, further comprising adjusting a position of at least one of the plurality of imaging detectors to change the FOV while acquiring the image data.

19. The method of claim 16, further comprising:
the positioning further comprising positioning the plurality of imaging detectors at initial positions;
the acquiring further comprising acquiring image data at the initial positions;
adjusting at least one of the plurality of imaging detectors to position the plurality of imaging detectors at second positions to change the FOV; and
acquiring image data with the plurality of imaging detectors at the second positions.

20. The method of claim 8, further comprising:
mounting a plurality of adjustable collimators on the plurality of imaging detectors; and
adjusting at least one of the adjustable collimators to define and adjust the FOV between first and second collimation positions.

21. The method of claim 16, further comprising adjusting at least one of an axial position and a radial position of at least one of the plurality of imaging detectors to change the FOV.

22. The method of claim 16, further comprising rotating at least one of the plurality of imaging detectors along at least one axis to change the FOV.

23. The method of claim 16, further comprising determining a pivot range for at least one of the plurality of imaging detectors, the pivot range identifying an amount for the at least one of the plurality of imaging detectors to move while acquiring the imaging data.

24. The method of claim 16, wherein the plurality of imaging detectors further comprises a first imaging detector, the method further comprising:
detecting outer edges of the structure of interest with the first imaging detector; and
determining a range of movement for the first imaging detector to scan the structure of interest.

25. An apparatus for imaging a structure of interest, comprising:
a plurality of imaging detectors mounted on a gantry, each of the imaging detectors having a field of view (FOV) and being independently movable with respect to each other to change the FOV, at least a sub-set of the plurality of imaging detectors being positioned to image a structure of interest within a patient;
a plurality of configurable collimators mounted and adjustable relative to the plurality of imaging detectors;
a collimator controller adjusting at least one of the plurality of configurable collimators, between first and second collimation positions, to change the FOV of at least one of the plurality of imaging detector; and
a data acquisition system for receiving image data detected within the FOV of the plurality of imaging detectors.

26. The apparatus of claim 25, further comprising a plurality of pivots interconnecting the gantry and at least one of the plurality of imaging detectors, the plurality of pivots moving the plurality of imaging detectors to change the FOV.

27. The apparatus of claim 25, further comprising a collimator controller adjusting an initial position of at least one of the plurality of configurable collimators to change the FOV.

28. The apparatus of claim 25, at least one of the plurality of configurable collimators further comprising strips of material arranged along first and second directions, the first and second directions being different with respect to each other, the strips of material being adjustable to change the POV.

* * * * *

UNITED STATES PATENT AND TRADEMARK OFFICE
CERTIFICATE OF CORRECTION

PATENT NO. : 7,592,597 B2
APPLICATION NO. : 11/498630
DATED : September 22, 2009
INVENTOR(S) : Hefetz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 315 days.

Signed and Sealed this

Twenty-first Day of September, 2010

David J. Kappos
*Director of the United States Patent and Trademark Office*